(12) United States Patent
Toivola et al.

(10) Patent No.: US 7,368,607 B2
(45) Date of Patent: May 6, 2008

(54) TOREMIFENE CRYSTALLIZATION METHOD

(75) Inventors: Reijo Toivola, Keitele (FI); Tuomas Huuhtanen, Lempäälä (FI)

(73) Assignee: Orion Corporation, Espoo (FI)

( * ) Notice: Subject to any disclaimer, the term of this patent is extended or adjusted under 35 U.S.C. 154(b) by 0 days.

(21) Appl. No.: 10/557,471

(22) PCT Filed: May 19, 2004

(86) PCT No.: PCT/FI2004/000304

§ 371 (c)(1),
(2), (4) Date: Oct. 19, 2006

(87) PCT Pub. No.: WO2004/101492

PCT Pub. Date: Nov. 25, 2004

(65) Prior Publication Data

US 2007/0093556 A1    Apr. 26, 2007

(30) Foreign Application Priority Data

May 19, 2003   (FI)   ................... 20030747

(51) Int. Cl.
*C07C 215/46*   (2006.01)
(52) U.S. Cl. .................................... 564/346
(58) Field of Classification Search ............ None
See application file for complete search history.

(56) References Cited

U.S. PATENT DOCUMENTS

| | | |
|---|---|---|
| 4,696,949 A | 9/1987 | Kurkela et al. |
| 5,011,771 A | 4/1991 | Bellet et al. |
| 5,491,173 A | 2/1996 | Toivola et al. |
| 6,491,951 B1 | 12/2002 | Kananen et al. |

FOREIGN PATENT DOCUMENTS

| | | | |
|---|---|---|---|
| DK | 165785 | * | 1/1993 |
| EP | 0 095 875 | | 12/1983 |
| EP | 0 158 973 | | 10/1985 |

OTHER PUBLICATIONS

Chemical Abstract of DK165785: 1992:489944 , 1992.*
Abstract of DK 165 785 (Jan. 18, 1993).

\* cited by examiner

*Primary Examiner*—Samuel A Barts
(74) *Attorney, Agent, or Firm*—Finnegan, Henderson, Farabow, Garrett & Dunner, LLP

(57) ABSTRACT

The invention relates to a method for isolating toremifene from a mixture of toremifene and its corresponding E isomer. The method comprises contacting the isomer mixture with a first solvent comprising methanol, allowing toremifene to crystallize in said first solvent, allowing the crystallized product of the previous step to crystallize from a second solvent comprising acetone, methyl ethyl ketone or ethyl acetate, and optionally converting toremifene crystallized from the previous step to a pharmaceutically acceptable salt thereof.

18 Claims, No Drawings

TOREMIFENE CRYSTALLIZATION METHOD

This application is a U.S. national stage filing of PCT international application no. PCT/FI2004/000304, filed on May 19, 2004, which claims the benefit of priority to Finnish patent application no. 20030747, filed on May 19, 2003.

TECHNICAL FIELD

The invention relates a method of preparing toremifene which is a Z isomer of 4-chloro-1,2-diphenyl-1-[4-[2-(N,N-dimethylamino)ethoxy]phenyl]-1-butene or a pharmaceutically acceptable salt thereof. Particularly the invention relates to a method of isolating toremifene of high purity from a mixture of its geometric isomers.

BACKGROUND OF THE INVENTION

Toremifene, the Z isomer of 4-chloro-1,2-diphenyl-1-[4-[2-(,N-dimethyl-amino)ethoxy]phenyl]-1-butene, is a triphenylethylene derivative of formula

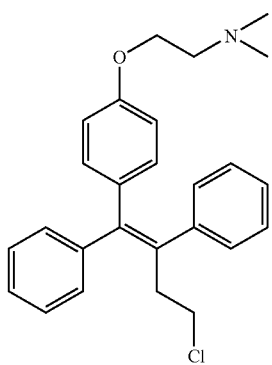

Toremifene has antiestrogenic activity and is useful in the treatment of hormone dependent breast cancer. Only the Z isomer has the useful antiestrogenic activity, the E isomer being estrogenic. Thus, the isomeric purity of toremifene is critical, since the presence of E-isomer may counteract the antiestrogenic effect of toremifene. A method for preparing toremifene, its analogs and salts has been described in U.S. Pat. No. 4,696,949. As described therein, toremifene can be conveniently prepared in a single step reaction by treating corresponding triphenyl diol compound with thionyl chloride, wherein a mixture of E and Z isomers is obtained. U.S. Pat. No. 4,696,949 describes separation of the E or Z isomers of toremifene analogs or their salts by crystallization from solvents such as hexane-ethanol (95:5), toluene-petrol ether (1:1) and toluene. However, it has been found that these methods have drawbacks related to the yield, purity or color of the end product. Thus, there is still a need for an improved method for isolating of substantially pure Z isomer of toremifene.

SUMMARY OF THE INVENTION

It has been found that toremifene or a pharmaceutically acceptable salt thereof can be prepared with an improved combination of yield, purity and color, if toremifene base is isolated from its corresponding E isomer in a two-step crystallization process the first solvent comprising methanol and the second solvent comprising acetone, methyl ethyl ketone or ethyl acetate. If desired, the toremifene base thus obtained can be converted to its pharmaceutically acceptable salt by conventional methods. It was found that separating the Z and E isomers after the formation of a salt is less advantageous. The method of the invention is simple, suitable for manufacturing on the large scale, and provides toremifene or its pharmaceutically acceptable salts of high quality.

DETAILED DESCRIPTION OF THE INVENTION

The present invention provides a method for isolating toremifene from any mixture comprising toremifene and its corresponding E isomer. Such mixture of Z and E isomers can be obtained for example using various methods described in U.S. Pat. No. 4,696,949. The mixture of isomers is preferably free of substantial amounts of other substances. The mixture of isomers is suitably a residue of a distillation, filtering or centrifugation process.

The method comprises the steps of (a) contacting a mixture of toremifene base and its corresponding E isomer with a first solvent comprising methanol; (b) allowing toremifene to crystallize in said first solvent; (c) allowing the crystallized product of the previous step to crystallize from a second solvent comprising acetone, methyl ethyl ketone or ethyl acetate; and (d) optionally converting toremifene crystallized from the previous step to a pharmaceutically acceptable salt thereof.

According to the invention, the mixture comprising toremifene base and its corresponding E-isomer is first contacted with the first solvent comprising methanol. The mixture may comprise equimolar amounts of the Z and E isomers or it may be enriched in one or other isomer. It is preferred that at least 80 w-%, preferably at least 90 w-%, more preferably at least 95 w-%, especially at least 99 w-%, of the first solvent is methanol.

The first solvent is used in amount sufficient to dissolve the Z and E isomers of the mixture. In the method, the Z and E isomers of the mixture are suitably dissolved in a sufficient amount of the first solvent by heating in a suitable reactor vessel. Advantageously, the first solvent is heated to its boiling point. The solution is preferably refluxed until the Z and E isomers of the mixture are completely dissolved. Solid purification aids such as celite or activated charcoal may be added to the mixture. In such case the solid material is removed from the hot solution before crystallization step, e.g. by pressure filtering. If desired, part of the solvent may be distilled off before crystallization.

The crystallization from the first solvent is suitably carried out by cooling the solution to a temperature which is less than the dissolution temperature used above. The crystallization from the first solvent is suitably carried out by cooling the solution to a temperature which is lower than 30° C., preferably lower than 20° C., more preferably lower than 10° C., and especially lower than 0° C. It is particularly preferred to carry out crystallization from the first solvent by cooling the solution to a temperature which is from about −15° C. to about 0° C., for example from about −10° C. to about −3° C.

The cooling is preferably carried out during 1 to 24 hours, typically during 2 to 10 hours, for example during 3 to 5 hours. The solution is preferably agitated in the crystallization temperature, preferably from 1 to 5 hours, typically from 1.5 to 2.5 hours.

The crystalline product enriched in Z isomer of toremifene can be recovered from the solution by conventional methods such as centrifugation or filtering. The washed crystalline product can be dried, if desired. However, it is preferred to transfer the recovered crystalline product directly to the next process step described below.

The recovered crystalline product enriched in Z isomer of toremifene is subsequently dissolved in the second solvent comprising acetone, methyl ethyl ketone or ethyl acetate in a suitable reactor vessel.

In case the second solvent comprises acetone, it is preferred that at least 80 w-%, preferably at least 90 w-%, more preferably at least 95 w-%, especially at least 99 w-%, is acetone. In case the second solvent comprises methyl ethyl ketone, it is preferred that at least 80 w-%, preferably at least 90 w-%, more preferably at least 95 w-%, especially at least 99 w-%, of the second solvent is methyl ethyl ketone. In case the second solvent comprises ethyl acetate, it is preferred that at least 80 w-%, preferably at least 90 w-%, more preferably at least 95 w-%, especially at least 99 w-%, of the second solvent is ethyl acetate. Acetone is the preferred second solvent.

The crystalline product enriched in Z isomer is suitably dissolved in the second solvent by heating. Advantageously, the second solvent is heated to its boiling point. The second solvent is used in an amount sufficient to dissolve the Z and E isomers of the mixture. The second solvent is preferably refluxed until the Z and E isomers of the mixture are completely dissolved. If desired, part of the second solvent may be distilled off before crystallization.

The crystallization from the second solvent is suitably carried out by cooling the solution to a temperature which is less than the dissolution temperature used above. The crystallization from the second solvent is suitably carried out by cooling the solution to a temperature which is lower than 30° C., preferably lower than 20° C., more preferably lower than 10° C., and especially lower than 0° C. It is particularly preferred to carry out crystallization by cooling the solution to a temperature which is from about −20° C. to about 0° C., more preferably from about −15° C. to about −5° C., for example from about −13° C. to about −7° C.

The cooling of the second solvent is preferably carried out during 1 to 24 hours, typically during 5 to 15 hours, for example during 8 to 12 hours. The solution is preferably agitated in the crystallization temperature, preferably from 1 to 5 hours, typically from 1.5 to 2.5 hours.

The crystalline toremifene base (Z isomer) can be recovered from the solution by conventional methods such as centrifugation or filtering. The crystalline product is washed and dried. Suitably the crystalline product is dried first at room temperature for about 0.5 hour and then at 45-55° C. for about two hours. After drying, the crystalline toremifene base of high purity is cooled to room temperature.

The pharmaceutically acceptable salts of toremifene with high purity can be prepared by contacting the above-obtained toremifene base with a selected salt in a suitable solvent using the procedures described in U.S. Pat. No. 4,696,949. The mixture is heated until all solids have dissolved, then cooled and the crystalline salt recovered and dried. Examples of suitable salts are salts with inorganic acids such as hydrochloric acid, hydrobromic acid or nitric acid, and salts with organic acids such as methanesulfonic acid, citric acid or tartaric acid. Toremifene citrate is the preferred salt.

Generally, the method according to the invention may be used to prepare toremifene or a pharmaceutically acceptable salt thereof comprising E isomer less than 1%, preferably less than 0.5%, more preferably less than 0.2%, and especially less than 0.15%, by weight.

EXAMPLES

Example 1

65 g of 1-[4-(2-dimethylaminoethoxy)phenyl]-1,2-diphenylbutane-1,4-diol was added to 515 ml of toluene. 40 ml of toluene was distilled from mixture in normal pressure. The mixture was then cooled to −7±3° C. 35 ml of thionyl chloride was added during 5±1 hours while keeping the mixture at −7±3° C. The mixture was stirred for 1 hour in −2±3° C. and then heated to 80° C. during three hours. The stirring was then continued for four hours in this temperature. The mixture was cooled to 50±5° C. and 125 ml of water and 75 ml of 50% NaOH was added. The layers were separated and water layer was discarded. Toluene layer was washed with 80 ml of water. Toluene layer was cooled and distilled off under a vacuum. Methanol (65 ml) was added to the residue and distilled off under a vacuum. The distillation residue comprised a mixture of toremifene base and its corresponding E-isomer. 195 ml of methanol, 1 g of celite and 1 g of activated charcoal was added to the residue and 15 ml of methanol was distilled from the mixture. The hot mixture was filtered in pressure filter and the celite/charcoal cake was washed with 10 ml of boiling methanol. The washing methanol and the filtrate was combined and heated to boiling. The solution was cooled to −7±3° C. during four hours and stirred for 3-5 hours. The precipitate was filtered and washed with 50 ml of methanol. The precipitate comprising partly purified toremifene base was dissolved in 95 ml of acetone by heating until boiling. The product was allowed to crystallize by cooling the mixture to −10±3° C. during 10 hours. The crystalline toremifene base was filtered and washed with 30 ml of acetone. The product was dried in vacuum in 50° C. Yield 26.08 g (40%).

Example 2

Partly purified toremifene base (5.0 g) obtained from methanol crystallization as described in Example 1 was dissolved in 20 ml of acetone, methyl ethyl ketone or ethyl acetate by heating to boiling and allowed to crystallize by cooling to −10° C. during 13 hours using the procedure of Example 1. The purity and color of the crystallized toremifene base product are summarized below.

TABLE 1

Purity (% of E-isomer) of toremifene base product crystallized first from methanol and then from acetone, methyl ethyl ketone or ethyl acetate.

| Second solvent | E-isomer impurity (%) | Purity/HPLC (%) |
|---|---|---|
| Acetone | 0.13 | 99.4 |
| Methyl ethyl ketone | 0.22 | 99.3 |
| Ethyl acetate | 0.17 | 99.3 |

The color of each crystaline product was good. In the analysis carried out according to the Degree of Coloration of Liquids, Ph. Eur. 2.2.2, Fourth Ed., (2002) the coloration of each product in solution was less than the coloration of the standard solution BY 3 of the method.

The invention claimed is:

1. A method for preparing toremifene or a pharmaceutically acceptable salt thereof, the method comprising the steps of (a) contacting a mixture comprising toremifene base and its corresponding E isomer with a first solvent comprising methanol; (b) allowing toremifene to crystallize in said first solvent; (c) allowing the crystallized product of the previous step to crystallize from a second solvent comprising acetone, methyl ethyl ketone or ethyl acetate; and (d) optionally converting toremifene crystallized from the previous step to a pharmaceutically acceptable salt thereof.

2. A method according to claim 1, wherein said first solvent comprises at least 80 w-% of methanol.

3. A method according to claim 1, wherein said second solvent comprises acetone.

4. A method according to claim 3, wherein said second solvent comprises at least 80 w-% of acetone.

5. A method according to claim 1, wherein said second solvent comprises methyl ethyl ketone.

6. A method according to claim 5, wherein said second solvent comprises at least 80 w-% of methyl ethyl ketone.

7. A method according claim 1, wherein said second solvent comprises ethyl acetate.

8. A method according to claim 7, wherein said second solvent comprises at least 80 w-% of ethyl acetate.

9. A method according to claim 1, wherein said pharmaceutically acceptable salt of toremifene is toremifene citrate.

10. A method according to claim 1, which comprises the step of converting the toremifene crystallized from the second solvent to a pharmaceutically acceptable salt.

11. A method according to claim 1, wherein said first solvent comprises at least 90 w-% of methanol.

12. A method according to claim 1, wherein said first solvent comprises at least 95 w-% of methanol.

13. A method according to claim 3, wherein said second solvent comprises at least 90 w-% of acetone.

14. A method according to claim 3, wherein said second solvent comprises at least 95 w-% of acetone.

15. A method according to claim 5, wherein said second solvent comprises at least 90 w-% of methyl ethyl ketone.

16. A method according to claim 5, wherein said second solvent comprises at least 95 w-% of methyl ethyl ketone.

17. A method according to claim 7, wherein said second solvent comprises at least 90 w-% of ethyl acetate.

18. A method according to claim 7, wherein said second solvent comprises at least 95 w-% of ethyl acetate.

* * * * *